United States Patent [19]

Maeda et al.

[11] Patent Number: 5,180,582

[45] Date of Patent: Jan. 19, 1993

[54] SUPEROXIDE DISMUTASE DERIVATIVES, A METHOD OF PRODUCING THE SAME AND MEDICINAL USES OF THE SAME

[75] Inventors: Hiroshi Maeda, 631-3, Aza-Tamukae, Hotakubohon-machi, Kumamoto City, Japan; Fujio Suzuki, Galveston, Tex.; Tatsuya Oda, Kumamoto, Japan

[73] Assignees: Hiroshi Maeda, Kumamoto; Kuraray Co., Ltd., Okayama, both of Japan

[21] Appl. No.: 836,861

[22] Filed: Feb. 19, 1992

Related U.S. Application Data

[62] Division of Ser. No. 199,809, May 27, 1988.

Foreign Application Priority Data

[30]

May 28, 1987 [JP] Japan .................. 62-134563

[51] Int. Cl.$^5$ ............................................. A61K 37/50
[52] U.S. Cl. .................................. 424/94.4; 424/94.1
[58] Field of Search .............................. 424/94.4, 94.1

Primary Examiner—Douglas W. Robinson
Assistant Examiner—Jean C. Witz
Attorney, Agent, or Firm—Burns, Doane, Swecker & Mathis

[57] ABSTRACT

The invention provides a superoxide dismutase derivative of the general formula

[SOD][Z]

wherein [SOD] represents a superoxide dismutase having 1 to 22 or 24 groups each derived from an amino groups by removal of one hydrogen atom in lieu of amino groups; [Z] represents a monovalent copolymer group, constituting units of which are a group of the formula

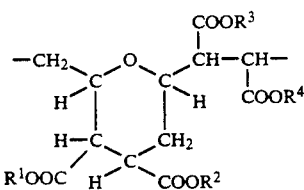

wherein $R^1$, $R^2$, $R^3$ and $R^4$ each represents a hydrogen atom or a residue derived by a removal of a hydroxyl group from an alkanol of 1 to 8 carbon atoms, an ethylene glycol monoalkyl ether containing an alkyl moiety of 1 to 4 carbon atoms or a glycerin dialkyl ether containing alkyl moieties of 1 to 4 carbon atoms, provided that either $R^1$ or $R^2$ and either $R^3$ or $R^4$ each represents a hydrogen atom, and a residue derived from the group of the above-mentioned formula by removal of $OR^1$, $OR^2$, $OR^3$ or $OR^4$ group from one of its $COOR^1$, $COOR^2$, $COOR^3$ and $COOR^4$ groups (where the bond on the carbon atom of the carbonyl group is attached to [SOD]), said monovalent copolymer group having an average molecular weight of 500 to 200,000; and n represents an integer of 1 to 22 or 24 corresponding to the number of said groups each derived from an amino group by removal of one hydrogen atom in said [SOD], or a pharmaceutically acceptable salt thereof. There also is provided a method for producing the above derivative and salt. The invention is further directed to medicinal uses and pharmaceutical compositions for oral administration.

5 Claims, 3 Drawing Sheets

SUPEROXIDE DISMUTASE DERIVATIVES, A METHOD OF PRODUCING THE SAME AND MEDICINAL USES OF THE SAME

This application is a divisional of application Ser. No. 07/199,809, filed May 27, 1988.

BACKGROUND OF THE INVENTION

1. Field of the Invention

The present invention relates to superoxide dismutase derivatives, a method of producing the same, medicinal uses for said derivatives, and compositions containing said derivatives for oral administration.

2. Description of Prior Art

It is known that superoxide dismutase (hereinafter referred to briefly as SOD) is omnipresent in the living tissues of animals, plants and microorganisms and is an enzyme decomposing superoxide which is harmful to living organisms. Recently, attempts have been made to utilize isolated SOD as an antiinflammatory agent (FARUMASHIA, 17, 411, 1981 and Current Therapeutic Research, 16, 706, 1974).

It is also known that when SOD is administered intravenously, its plasma half-life is as short as 4 to 6 minutes and that the administered SOD is rapidly excreted. For prolonging the plasma half-life of SOD, an attempt has been made to modify SOD with Ficoll, polyethylene glycol, rat albumin or inulin [Japanese Published Unexamined Patent Application (Kokai Tokkyo Koho) No. 32826/83].

It has been reported that the SOD activity of Ficoll- or polyethylene glycol-modified SOD is drastically lower than that of unmodified SOD, while rat albumin-modified SOD is antigenic. It has also been found that inulin-modified SOD is considerably inferior to SOD in enzymatic activity.

It is an object of the invention to provide a novel superoxide dismutase derivative having a remarkably extended plasma half-life as compared with SOD while retaining the enzymatic activity of SOD substantially intact.

It is another object of the invention to provide a novel superoxide dismutase derivative which has pharmacological actions such as antiinflammatory action and so on and is safe.

It is a still another object of the invention to provide a method of producing said superoxide dismutase derivative.

It is a further object of the invention to provide medicinal uses, for example as an antiinflammatory drug, of said superoxide dismutase derivative.

It is still another object of the invention to provide compositions suitable for oral administration of said superoxide dismutase derivative.

These objects as well as other objects and advantages of the present invention will become apparent to those skilled in the art from the following detailed description.

SUMMARY OF THE INVENTION

The present invention provides a superoxide dismutase derivative of the general formula

[SOD][Z]$_n$ wherein [SOD] represents a superoxide dismutase having 1 to 22 or 24 groups each derived from an amino group by removal of one hydrogen atom in lieu of amino groups; [Z] represents a monovalent copolymer group, constituting units of which are a group of the formula

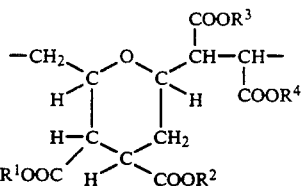

wherein $R^1$, $R^2$, $R^3$ and $R^4$ each represents a hydrogen atom or a residue derived by removal of a hydroxyl group from an alkanol of 1 to 8 carbon atoms, an ethylene glycol monoalkyl ether containing an alkyl moiety of 1 to 4 carbon atoms or a glycerin dialkyl ether containing alkyl moieties of 1 to 4 carbon atoms, provided that either $R^1$ or $R^2$ and either $R^3$ or $R^4$ each represents a hydrogen atom, and a residue derived from the group of the above-mentioned formula by removal of $OR^1$, $OR^2$, $OR^3$ or $OR^4$ group from one of its $COOR^1$, $COOR^2$, $COOR^3$ and $COOR^4$ groups (where the bond on the carbon atom of the carbonyl group is attached to [SOD]), said monovalent copolymer group having an average molecular weight of 500 to 200,000; and n represents an integer of 1 to 22 or 24 corresponding to the number of said groups each derived from an amino group by removal of one hydrogen atom in said [SOD], or a phamaceutically acceptable salt thereof.

The present invention further provides a method of producing the above superoxide dismutase derivative (hereinafter referred to briefly as SOD) or the pharmaceutically acceptable salt thereof, which comprises reacting superoxide dismutase with a copolymer, constituent units of which are:

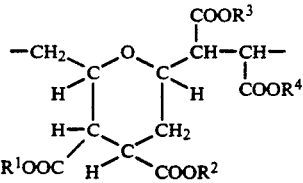

wherein $R^1$, $R^2$, $R^3$ and $R^4$ each represents a hydrogen atom or a residue derived by removal of a hydroxyl group from an alkanol of 1 to 8 carbon atoms, an ethylene glycol monoalkyl ether containing an alkyl moiety of 1 to 4 carbon atoms or a glycerin dialkyl ether containing alkyl moieties of 1 to 4 carbon atoms, provided that either $R^1$ or $R^2$ and either $R^3$ or $R^4$ each represents a hydrogen atom, and (b) a group selected from the class consisting of a group of the formula

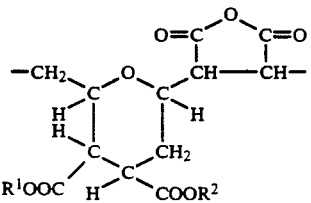

wherein $R^1$ and $R^2$ are respectively as defined above, a group of the formula

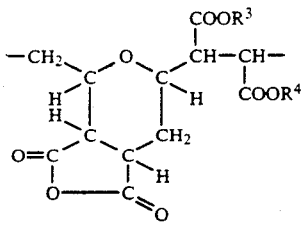

wherein $R^3$ and $R^4$ are respectively as defined above and a group of the formula

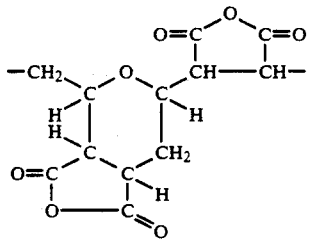

said copolymer having an average molecular weight of 500 to 200,000 (hereinafter referred to briefly as the copolymer) in the presence of a basic aqueous solution of pH 7–11.

The present invention provides, in another aspect, a pharmaceutical composition such as an antiinflammatory agent which contains said SOD derivative or a salt thereof as an active ingredient and a method for treatment of inflammatory and other diseases which comprises administering an effective amount of said SOD derivative or salt thereof.

In a further aspect, the present invention provides a pharmaceutical composition for oral administration which comprises said SOD derivative or a salt thereof and a medium/higher fatty acid glyceride, and a pharmaceutical composition for oral administration which comprises said SOD derivative or a salt thereof, a medium/higher fatty acid glyceride, and an amphiphilic agent and/or a lower alkanol.

Figure 1:
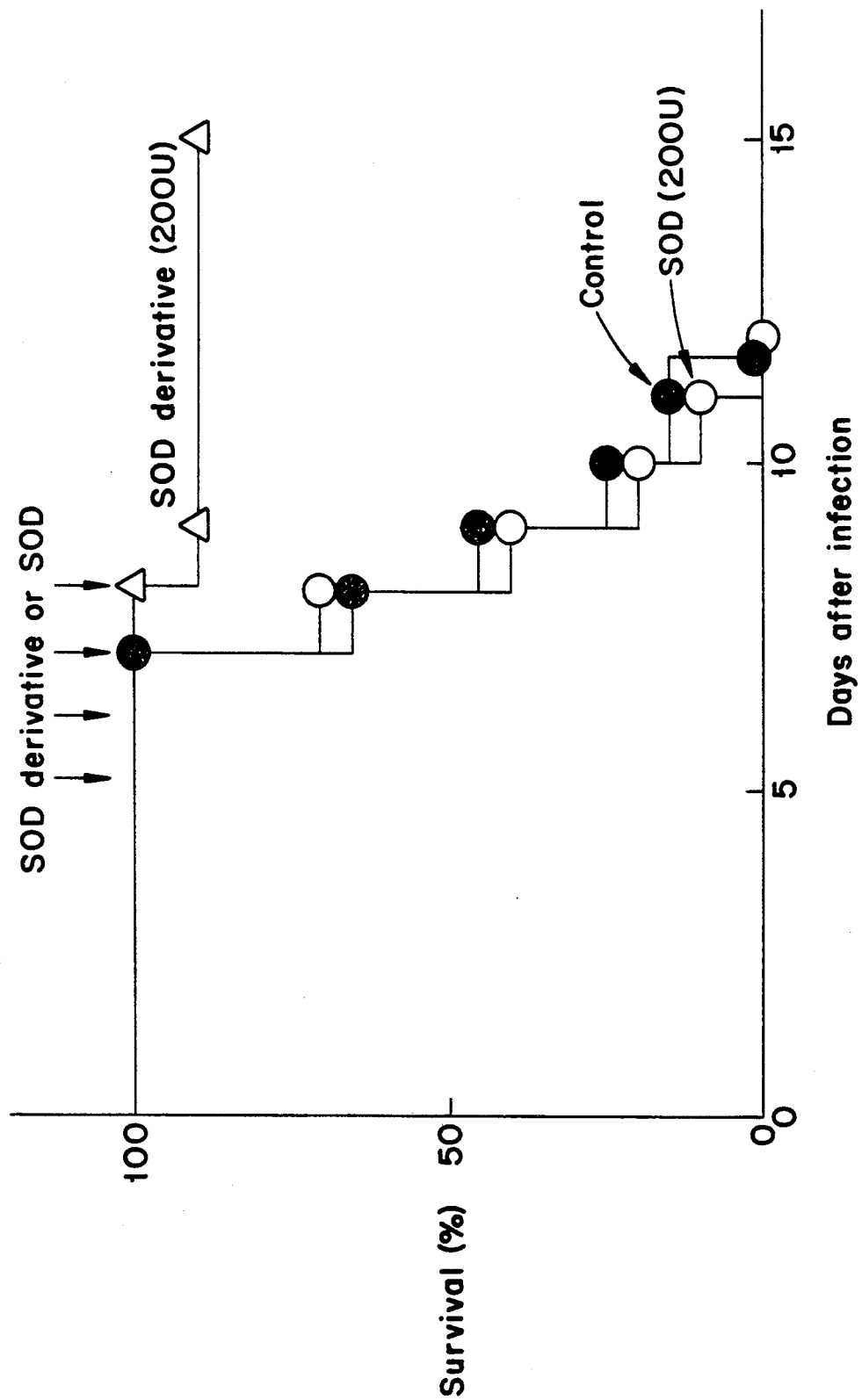
FIG. 1 shows the effect of the SOD derivative and SOD on influenza virus infected mice.

DETAILED DESCRIPTION OF THE INVENTION (a) Method for Production of the SOD Derivative (a-1) Reaction of SOD with the Copolymer The reaction of SOD with the copolymer is generally conducted by dissolving SOD in an aqueous solution of a salt such as sodium carbonate, sodium hydrogen carbonate, sodium acetate, sodium phosphate, etc. and adding the copolymer, either in powder form or as dissolved in an organic solvent such as dimethyl sulfoxide, to the resulting solution. It is necessary that the pH of the solution be maintained in the range of 7 to 11 during the reaction. If the pH is below 7, the solubility of the copolymer is decreased to interfere with progress of the reaction. If the pH is higher than 11, the SOD is inactivated so that an effective SOD derivative cannot be obtained. The reaction temperature is preferably about 3° to 50° C. and, for still better results, in the range of 3° to 40° C. While the reaction time is dependent on the reaction temperature and the method of addition of the copolymer, it is generally in the range of 10 minutes to 3 hours. The proportion of the copolymer is in the range of about 0.5 to 30 moles to 1 mole of SOD. By varying this ratio, the number of molecules of the copolymer to be attached to SOD can be adjusted.

The resulting reaction mixture contains not only the SOD derivative but also the unreacted SOD and copolymer, etc. Therefore, the reaction mixture is filtered and the filtrate is subjected to gel filtration. The resulting filtrate containing the SOD derivative is subjected, if necessary, to hydrophobic chromatography and to ultrafiltration. The concentrate thus obtained is freeze-dried to give the SOD derivative as a solid product.

As the result of the reaction described above, the amino groups of SOD are bound to the maleic anhydride moieties of the copolymer to give the SOD derivative. For example, human type SOD contains 22 (human erythrocyte SOD or genetically engineered human-type SOD produced by yeast) or 24 (genetically engineered human-type SOD produced by *Escherichia coli*) amino groups per molecule. In the above reaction, a certain one of said amino groups of SOD reacts with one of the maleic anhydride moieties of the copolymer to ultimately give a SOD derivative containing 1 to 22 or 24 molecules of the copolymer per molecule of the SOD. The starting material copolymer generally contains maleic anhydride rings as described later. When one of these maleic anhydride rings is bound to an amino group of SOD, the remaining maleic anhydride ring does not react appreciably with another amino group but tends to react with water, giving rise to a maleic acid-derived group of the formula

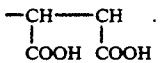

It is possible that one molecule of the copolymer reacts with a plurality of molecules of SOD to give a by-product compound in which a plurality of maleic anhydride rings in the copolymer molecule are bound to amino groups of the respective SOD molecules but it is not objectionable to use the SOD derivative including a small proportion of such byproduct in the practice of the invention. However, in consideration of the fact that any active ingredient of a pharmaceutical product is desirably a compound having a single chemical structure, it is preferable to purify the byproduct-rich SOD derivative by a suitable procedure such as gel filtration so as to remove the byproduct. Furthermore, it should be understood that the SOD derivative obtained by the above reaction is actually a mixture of compounds containing different numbers of molecules of the copolymer, that is to say the number of molecules of the copolymer bound to SOD is not uniform over the respective SOD derivative compounds. Therefore, in the above general formula representing the SOD derivative, n means the average number of molecules of the copolymer bound to one molecule of SOD. However, when it is desirable to obtain the SOD derivative in which the number of molecules of the copolymer bound to SOD is uniform, the SOD derivative obtained by the above method may be further subjected to a suitable fractional purification procedure such as gel filtration to give the desired SOD derivative.

(a-2) The Starting Material SOD

The SOD used as a starting material may be one extracted from the living tissue of an animal (man, cattle, etc.), plant or microorganism by the conventional procedure or one obtained by a genetic engineering method. The chemical structure (coordinating metal, molecular weight, amino acid sequence, etc.) of SOD has by now been elucidated fairly well. Thus, SOD has been classified into the three major types of Fe- coordinating SOD, Mn-coordinating SOD and Cu.Zn-coordinating SOD and, depending on the biological tissue in which it occurs, has a molecular weight in the range of 30,000 to 80,000. While the amino acid sequence of SOD also varies somewhat with different biological tissues in which it is contained, detailed information on this subject can be obtained from the following literature: Yoshihiko Oyanagi: Superoxide and Medicine, 74-90 (Kyoritsu Shuppan, May 25, 1981); Journal of Biological Chemistry, 246, 2875-2880 (1971); and 250, 6107-6112 (1975); Proceedings of the National Academy of Sciences, 70, 3725-3729 (1973); Archives of Biochemistry and Biophysics, 179, 243-256 (1977) and so on. The starting material SOD is preferably a human-type Cu.Zn-coordinating SOD. The bovine- and equine-type Cu.Zn-coordinating SODs are also suitable for the purposes of the invention. This kind of SOD has a molecular weight of about 33,000 and contains 20, 22 or 24 amino groups in its molecule. The human type SOD can, for instance, be isolated by subjecting human blood to heat treatment, ion exchange and gel filtration in succession or by a genetic engineering method.

(a-3) The Starting Material Copolymer

The copolymer as another starting material can be obtained by subjecting a divinyl ether-maleic anhydride copolymer to partial hydrolysis (degree of hydrolysis of maleic anhydride rings: 30-90%) or subjecting said copolymer to partial half-esterification (degree of half-esterification of maleic anhydride rings: 30-90%). As examples of the ester, there may be mentioned methyl ester, ethyl ester, propyl ester, n-butyl ester, n-pentyl ester, isopentyl ester, n-hexyl ester, n-heptyl ester, n-octyl ester, methoxyethyl ester, ethoxyethyl ester, propoxyethyl ester, 2-butoxyethyl ester, 1,3-dimethoxy-2-propyl ester, 2,3-dimethoxy-1-propyl ester, 1,3-diethoxy-2-propyl ester, 2-ethoxy-3-methoxy-1-propyl ester, 1,3-dipropoxy-2-propyl ester, 1,3-dibutoxy-2-propyl ester, benzyl ester and so on.

The starting material copolymer has, as aforesaid, a weight average molecular weight in the range of 500 to 200,000. In view of the transfer kinetics of the final SOD derivative to the affected site in vivo, the weight average molecular weight of the copolymer is preferably not over 10,000. There is no particular limitation on the molecular weight distribution of the copolymer. Thus, the copolymer (whose weight average molecular weight/number average molecular weight ratio is about 2.0 or higher) synthesized by the radical copolymerization of divinyl ether with maleic anhydride and directly subjected to partial hydrolysis or partial half-esterification without prior fractionation or after fractionation for narrowing its molecular weight distribution can be successfully employed as the starting material copolymer.

(b) The Pharmaceutically Acceptable Salt of SOD Derivative, and a Process for Preparation of the Salt.

As examples of the aforesaid pharmaceutically acceptable salt of SOD derivative, there may be mentioned the salts of the derivative with alkali metals such as sodium, potassium, etc., salts with alkaline earth metals such as magnesium, calcium, barium, etc., ammonium salt, and salts with tertiary amines such as pyridine, triethylamine, tri-n-butylamine and so on.

The pharmaceutically acceptable salt of SOD derivative can be easily prepared from the SOD derivative and the desired kind of base by the routine salt forming reaction.

(c) Compositions for Oral Administration

The medium/higher fatty acid glyceride which is used for preparation of the composition for oral administration according to the invention is the mono-, di- or triglyceride of a saturated or unsaturated fatty acid containing 6 to 20 carbon atoms. Representative examples of such fatty acid glyceride include the mono-, di- and triglycerides of caprylic acid, capric acid, lauric acid, myristic acid, palmitic acid, oleic acid, linoleic acid, linolenic acid or the like. These fatty acid glycerides can be used singly or in combination.

The fatty acid glyceride may be a naturally-occuring compound or a synthetic or semi-synthetic compound. Usually, it is expedient to employ a natural vegetable oil. The vegetable oils which can be employed with advantage in the practice of the invention include, among others, olive oil (oleic acid 70-80%, linolic acid 4-12%, palmitic acid 7-15%), maize oil (linolic acid 40-60%, palmitic acid 25-45%), sesame oil (oleic acid 35-46%, linolic acid 35-48%), camellia oil, coconut oil (lauric acid 45-52%, capric acid 4-12%, caprylic acid 6-10%) and palm oil. Commercial products can be used as such. Thus, for example, commercially available medium fatty acid triglycerides such as Panasate ® 875, 810 and 800 (Nippon Oil and Fats Co., Ltd.; caprylic acid content 10-100%), ODD ® (Nissin Seiyu K.K.; caprylic acid content 67%), etc. can be utilized. As an example of commercial medium fatty acid monoglyceride, there may be mentioned Homoteks ®PT (Kao Corporation; capric acid content 60%). As an example of medium fatty acid mono- and di- glyceride mixture, there may be mentioned Witafrol ® (Dinamit Novel Corporation). As for higher fatty acid triglyceride, commercial edible oils such as olive oil from Wako Pure Chemical Industries Ltd. and linolic acid from Nippon Oil and Fats Co., Ltd. can be utilized.

The aforesaid amphiphilic agent is a non-toxic agent having both hydrophilicity and lipophilicity. Typical examples of such amphiphilic agent include natural amphoteric surfactants, polyglycerin fatty acid ester, polyoxyethylene-sorbitan fatty acid ester (Tween series), sorbitan fatty acid ester (Span series) and polyethylene glycol. Preferred amphoteric surfactants are soybean phospholipid, yolk lecithin and their related substances, such as commercial phosphatidylcholine, yolk lecithin, soybean lecithin, phosphatidylethanolamine, etc. available from Nippon Oil and Fats Co., Ltd. The polyglycerin fatty acid ester may for example be Unigli ® (Nippon Oil and Fats Co., Ltd). As an example of the polyoxyethylene sorbitan fatty acid ester, there may be mentioned Tween ®20 (Wako Pure Chemical Industries, Ltd.). The sorbitan fatty acid ester may for example be Span ®20 (Wako Pure Chemical Industries, Ltd.), while the polyethylene glycol may be PEG 6000, for instance. Aside from the above, anionic surfactants such as sodium laurylsulfate and cationic surfactants such as benzalkonium chloride, benzethonium chloride, Eison ® (Nelson Research & Development Co., U.S.A.), etc. can also be employed The aforesaid alkanol may for example be ethanol, propanol, isopropyl alcohol, butanol or the like.

In the production of a composition according to the invention, a lyophilizate from aqueous solution of SOD derivative or its pharmaceutically acceptable salt (hereinafter referred to collectively as SOD derivative) adjusted to an appropriate pH is uniformly dispersed in said fatty acid glyceride containing, or not containing, said amphiphilic agent and/or lower alkanol or, alternatively, a mixture of a solution of SOD derivative in aqueous ammonium carbonate solution and an aqueous solution of said amphiphilic agent and/or lower alkanol is lyophilized and the lyophilizate is uniformly dispersed in the medium/higher fatty acid glyceride.

The proportion of said fatty acid glyceride is about 0.1 to 100 ml per mg of the SOD derivative and preferably about 0.5 to 5 ml on the same basis. The addition of said amphiphilic agent and/or lower alkanol is optional but these agents contribute to enhanced wettability with the oil and increased dispersibility or solubility therein so as to give a stable composition with an additional effect of enhanced absorption after oral administration. The proper level of addition of said amphiphilic agent varies with different species thereof. Generally, however, with respect to 1 mg of SOD derivative, it is appropriate to employ 0.01 to 0.1 ml when the amphiphilic agent is a liquid or 0.05 to 5 mg when it is a solid agent. The level of addition of said lower alkanol may be about 1 to 15 weight percent based on the total weight of the composition. The addition of such lower alkanol leads to an improved homogeneity of the solution.

The composition according to the invention is a clear liquid which is stable physically and chemically. Thus, when the composition was centrifuged at 5000 rpm for 15 minutes at room temperature or allowed to stand at 37° C. for 1 month, no sedimentation was observed. Furthermore, when stored in the dark at 4° C. or at room temperature, the composition of the invention showed no macroscopic change for at least 3 months. In addition, no macroscopic change was observed even after the composition was subjected to 10 cycles of temperature variation from 4° C. to room temperature at 24-hour intervals and its titer remained unaffected.

(d) Pharmacological Profile of the SOD Derivative

The SOD derivative according to the invention features a remarkably extended plasma half-life as compared with SOD while retaining the enzymatic activity of SOD substantially intact and is, furthermore, low in toxicity. Therefore, the SOD derivative of the invention is of value as an antiinflammatory agent and an agent for ischemic diseases.

The following animal experiments illustrate the effects of the SOD derivative and composition of the invention.

(I) ANTIINFLAMMATORY AND ANTIVIRUS EXPERIMENTS (1) Effect on Pulmonary Consolidation (Inflammatory Sclerosis) in Influenza-infected Mice Method ddY mice aged 5–6 weeks and weighing about 22 g were infected with influenza virus [A2/Kumamoto $(H_2N_2)$] in a dose of 100 times the $LD_{50}$ in mice by inhalation of a virus aerosol and, then, the test agent was orally administered in predetermined doses once a day for 6 consecutive days from the day of infection. The mice were used in groups of 30. The mice were serially sacrificed 3, 4 and 5 days after infection and the mouse pulmonary consolidation scores were determined by the method of Horsfall (Journal of Experimental Medicine, 95, 135–145, 1952).

The results are shown in Table 1. The consolidation scores in the table were determined as follows. Physiological saline was injected directly into the mouse heart to wash the lung thoroughly and the lung was then observed. The lesion was evaluated using the following scoring scale.

| Consolidation score | Percentage of consolidation in lung field |
| --- | --- |
| 0 | 0 |
| 0.5 | 12.5 |
| 1.0 | 25 |
| 1.5 | 37.5 |
| 2.0 | 50 |
| 2.5 | 62.5 |
| 3.0 | 75 |
| 3.5 | 87.5 |
| 4.0 | 100 |
| 5.0 | Death due to infection |

TABLE 1

| Test agent | Time (in days) after infection with influenza virus | | |
| --- | --- | --- | --- |
| | 3 | 4 | 5 |
| Physiological saline (control) | 0.67 | 0.89 | 1.33 |
| ODO ® alone (control) | 0.61 | 0.91 | 1.39 |
| SOD derivative of Example of Synthesis 1* (2,000 units/mg) | 0.0 | 0.17 | 0.33 |
| Composition of Formulation Example 6** (2,000 units/mg) | 0.0 | 0.11 | 0.15 |

*An aqueous solution
**An oily composition (2) Effect on Virus Infected Mice

Method ddY mice aged 5–6 weeks and weighing about 22 g were infected with influenza virus [$A_2$/Kumamoto $(H_2N_2)$] in a dose of 2 times the $LD_{50}$ in mice by inhalation of a virus aerosol and, then, the SOD derivative of Example of Synthesis 1 (2000 units/mg) or bovine erythrocyte SOD (2000 units/m9) was intravenously administered in a dose of 200 units/mouse once a day for 4 consecutive days from the 5th day after infection.

FIG. 1 shows % survival plotted against days after infection. The % survival was 95% in the SOD derivative group, and 0% in the SOD group and in the control group (infected and not treated mice). In a further test, the SOD was administered in a dose of 2000 units/- mouse in the same manner as above, and only a slight effect was observed.

It is evident from the results that the SOD derivative has an excellent effect on influenza virus infected mice.

(3) Effect on Albumin Leakage at the Site of Burn

Method

Evan's blue was dissolved in physiological saline at a final concentration of 0.2 weight % and 0.18 ml (10 mg/kg) of the solution was administered intravenously to ddY mice aged 8-10 weeks and weighing about 30 g. The mice were used in groups of 10. After administration, the head (12 mm diameter) of an iron nail preheated in a water bath at 70° C. was pressed against the abdomen of the mouse to cause a burn and the test agent was orally administered immediately. Two hours after administration of the test agent, the mice were sacrificed and the skin at the site of burn was excised and immersed in formamide at 60° C. for 48 hours. The concentration of extracted Evans' blue was determined based on the absorbance at 620 nm. The concentration of the Evans' blue-albumin complex was estimated from the data and the % inhibition of albumin leakage at the site of burn due to the test agent was calculated.

The results are shown in Table 2.

TABLE 2

| Test agent | Dosage (units/mouse) | Concentration of Evans' blue-albumin complex (μg/g protein) | Percent Inhibition |
|---|---|---|---|
| Physiological saline (control) | 0 | 82.0 | — |
| ODO ® alone (control) | 0 | 87.3 | 0 |
| SOD derivative of Example of Synthesis 1* (2,000 units/mg) | 400 | 41.3 | 49.6 |
| Composition of Formulation Example 6** (2,000 units/mg) | 400 | 38.1 | 53.5 |

*An aqueous solution
**An oily composition

The above experiment was repeated except that the mice were sacrificed 6 hours after administration. Then, in the same manner as above, the concentration of Evans' blue-albumin complex was determined. The % inhibition of albumin leakage at the site of burn was 0% in the ODO ® alone group, 50.0% in the SOD derivative (Example of Synthesis 1) group, and 56.5% in the SOD composition (Formulation Example 6) group.

The same result was obtained with the SOD derivative according to Example of Synthesis 2.

It will be apparent from the above results that the SOD derivative and composition of the invention significantly inhibited the albumin leakage at the site of burn as compared with the control groups.

(II) EXPERIMENT OF THE BLOOD TRANSFER OF THE SOD DERIVATIVE COMPOSITION AFTER ORAL ADMINISTRATION

The blood SOD derivative concentration was determined by radioactivity assay. The experimental procedures and results are given below.

Preparation of $^{14}C$ Glycine-labeled SOD Derivative

In 1.5 ml of distilled water was dissolved 17.7 mg of the SOD derivative according to Example of Synthesis 1, followed by addition of 18.2 mg of water-soluble carbodiimide. After 5 minutes, 0.13 mg (0.5 ml aqueous solution) of $^{14}C$ glycine (New England Nuclear, U.S.A.; 113.0 mCi/mmole) was added. The pH of the mixture was adjusted to about 6 with 1M aqueous sodium hydrogen carbonate solution and the reaction was allowed to proceed under gentle stirring at room temperature in the dark for 1 hour. Then, 1.0 ml of 1M acetate buffer (pH 6.0) was added so as to terminate the reaction and the reaction mixture was desalted with a column (2.3×10 cm) of Sephadex ®G-25 (Pharmacia F.C.) and lyophilized. The procedure gave 15.5 mg of $^{14}C$ glycine-labeled SOD derivative with a specific radioactivity of 10.7 μCi/mg. This product was a substantially uniform product mainly containing one glycine unit per molecule of SOD derivative. This product was a stable compound in which glycine had been bound by amide linkage to the carboxyl group of the SOD derivative.

(2) Oral Administration Experiment in Animals

Using the $^{14}C$ glycine-labeled SOD derivative, a composition was prepared in accordance with the method described hereinafter in Formulation Example 2 and using a gastric tube, 0.2 ml (4.26 μCi) of the composition was orally administered to male ddY mice aged 8 weeks. The mice were sacrificed serially at 3, 7 and 24 hours after administration and the radioactivity levels in the plasma and major organs were determined. The radioactivity was expressed in dpm per 1.0 g of tissue. The results are shown in Table 3.

TABLE 3

| Tissue | Time course of tissue concentration of $^{14}C$ glycine-labeled SOD derivative after oral administration | | |
|---|---|---|---|
| | After 3 hr | After 7 hr | After 24 hr |
| Plasma | 9304 | 7912 | 9908 |
| Liver | 32048 | 50224 | 90027 |
| Kidney | 12054 | 28465 | 62873 |
| Spleen | 5912 | 10392 | 22644 |
| Muscle | 2490 | 3452 | 12200 |

The data in Table 3 show that the composition containing the SOD derivative prepared in Example of Synthesis 1 is efficiently transferred to the blood and various organs and tissues. The same result was also obtained with a similar composition containing the SOD derivative obtained in Example of Synthesis 2.

Thus, the SOD derivative of the invention, when formulated into the composition of the invention and administered orally, produces particularly remarkable antiinflammatory effects.

For clinical application of the above composition to humans, the composition can be further processed into suitable dosage forms such as soft capsules, capsules, tablets, granules, liquids, suppositories, etc. and administered to patients.

Such preparations are generally administered in a dose of 0.1 to 100 mg (as SOD derivative) 1 to 5 times a day, either every day or every other day. The dosage is adjusted according to the patient's condition and other factors.

(e) EXAMPLES

The following synthesis and formulation examples are further illustrative of the invention, it being to be understood, however, that the invention is by no means limited to these specific examples.

EXAMPLE OF SYNTHESIS 1

In 10 ml of 0.1M aqueous sodium hydrogen carbonate solution (pH 8.0) was dissolved 95 mg of bovine erythrocyte SOD (Sigma) with stirring at 4° C. To this solution was gradually added 17 mg of a solid powder of partial hydrolyzate (degree of hydrolysis=about 50%) of a divinyl ether-maleic anhydride copolymer (divinyl ether to maleic anhydride mole ratio=1:2, $\overline{M}w$=5,600, molecular weight distribution:$\overline{M}w/\overline{M}n$=about 1.5) ($\overline{M}w$=weight average molecular weight, $\overline{M}n$ =number average molecular weight) and the reaction was conducted for about 1.0 hour. The reaction mixture was poured into a column (4.2×80 cm) of Sephadex ®G-50 (Pharmacia F.C.) for gel filtration and elution was carried out with distilled water. The eluate was monitored by the absorbance method at 280 nm and 220 nm and the fraction containing the unreacted divinyl ether-maleic anhydride copolymer partial hydrolyzate was discarded. The remaining fraction was lyophilized to give the SOD derivative as a white power.

Figure 2:
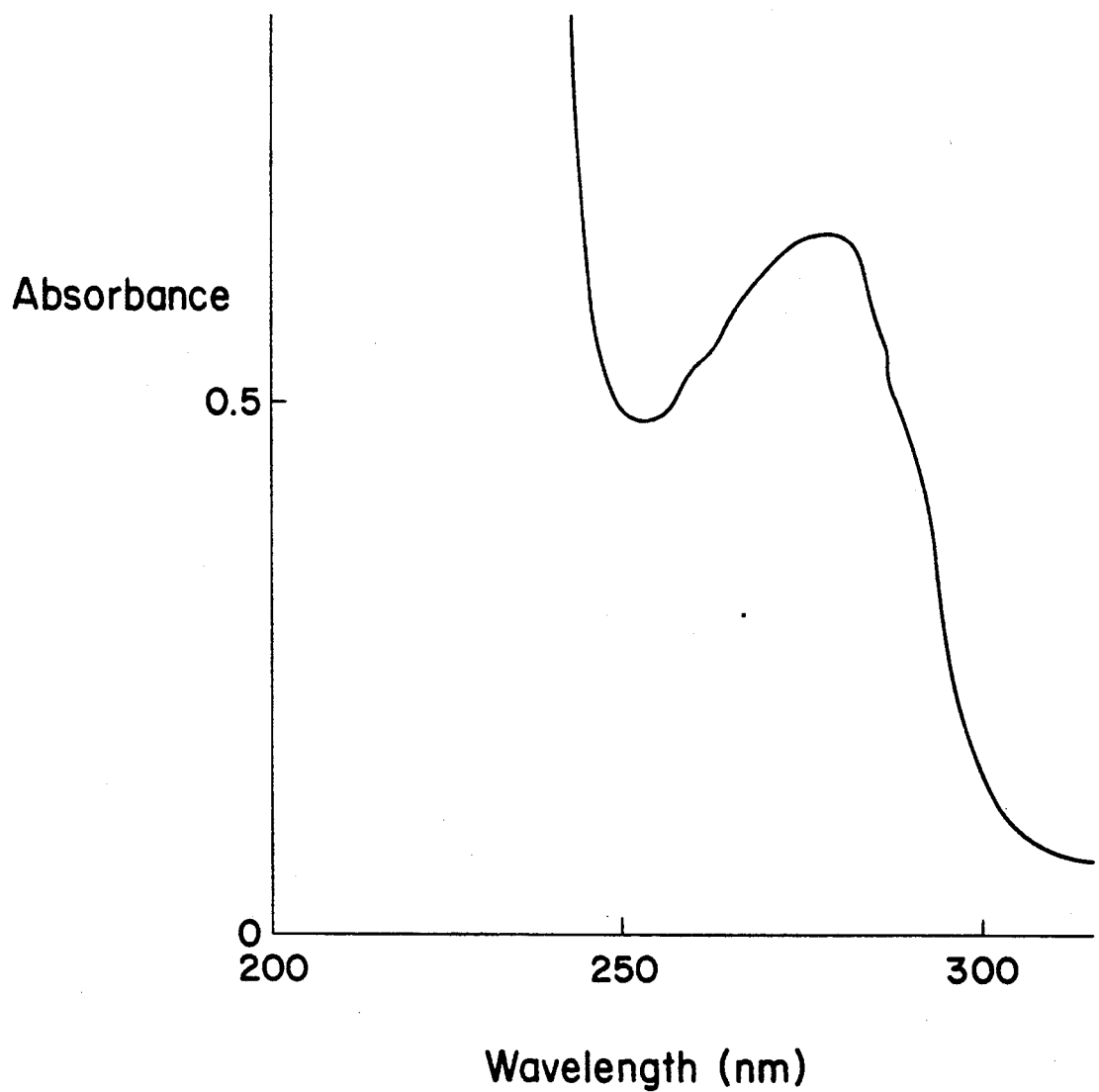
FIG. 2 is an ultraviolet absorption spectrum of the SOD derivative prepared in Example of Synthesis 1.

The ultraviolet absorption spectrum of the SOD derivative thus obtained was measured in phosphate buffer at the concentration of 1 mg/ml and pH 7.4. The UV absorption spectrum of this product is shown in FIG. 2.

The bovine erythrocyte SOD used above contained 20 amino groups per molecule In order to confirm that these amino groups had reacted with the partial hydrolyzate of divinyl ether-maleic anhydride copolymer, the assay of residual amino groups was performed using sodium trinitrobenzenesulfonate (TNBS). It was found that under the above conditions of reaction, about 22 mole % of the amino groups of bovine erythrocyte SOD had reacted so that an average of 4 to 5 molecules of the divinyl ether-maleic anhydride copolymer partial hydrolyzate were bound to each molecule of SOD.

When the enzymatic activity of the SOD derivative was determined by the pyrogallol auto-oxidation method described in European Journal of Biochemistry, 47, 469–474, 1974, the SOD derivative was found to retain 45% of the enzymatic activity of the original SOD.

EXAMPLE OF SYNTHESIS 2

(a) Synthesis of Partially Half-esterified Divinyl Ether-maleic Anhydride Copolymer A 100 ml (approx.) ampule with a magnetic stirrer was charged with 2.0 g of divinyl ether-maleic anhydride copolymer (divinyl ether to maleic anhydride mole ratio =1:2, $\overline{M}w$=5600, molecular weight distribution: $\overline{M}w/\overline{M}n$=1.5), 0.88 g of n-butanol, 40 mg of anhydrous lithium acetate and 60 ml of tetrahydrofuran, followed by sealing. The contents of the ampule were heated with stirring at 55° C. for 20 hours. An aliquot of the reaction mixture was sampled and the unreacted n-butanol in the reaction mixture was estimated by gas chromatography using ethyl-cellosolve as an internal standard. From the reaction rate of charged n-butanol, the degree of conversion of the maleic anhydride ring of the copolymer to the n-butyl half-ester was calculated to be 43.3 mole %. The reaction mixture was then concentrated under reduced pressure and the concentrate was added dropwise into 500 ml of n-hexane for reprecipitation. The resulting precipitate was recovered and dried at room temperature overnight to give 1.13 g of the desired n-butyl half-esterified divinyl ethermaleic anhydride copolymer.

Figure 3:
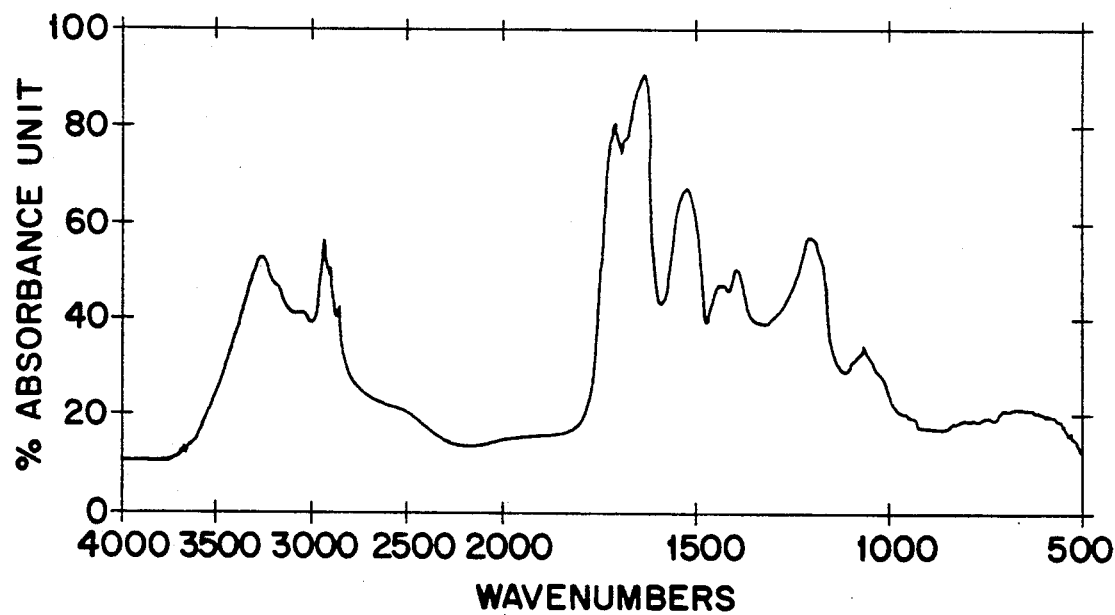
FIG. 3 is an infrared absorption spectrum of the SOD derivative prepared in Example of Synthesis 2.
Figure 4I:
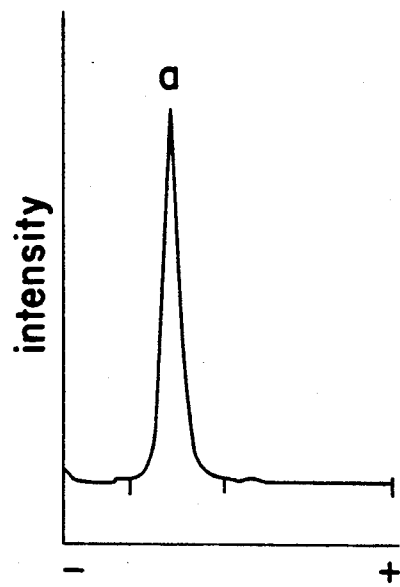
FIG. 4 (i) is a densitogram as measured by polyacrylamide electrophoresis of the starting material SOD used in Example of Synthesis 2, and FIG. 4 (ii) is a densitogram as measured by polyacrylamide electrophoresis of the SOD derivative prepared in Example of Synthesis 2.
Figure 4:
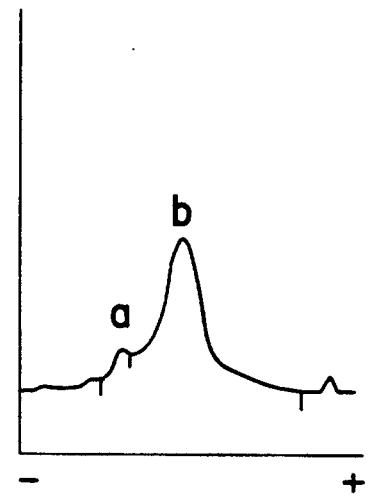

(b) Synthesis of the SOD Derivative by Reaction of N-butyl Half-esterified Divinyl Ether-maleic Anhydride Copolymer with SOD In 1.8 ml of isotonic phosphate buffer (pH 7.04) were dissolved 200 μl of aqueous human erythrocyte SOD solution (62.8 mg/ml) and 170 mg of sodium hydrogen carbonate. To this solution was gradually added 64 mg of the n-butyl half-esterified divinyl ether-maleic anhydride copolymer prepared as above (a) with stirring at room temperature. The reaction was conducted for 2 hours and, then, allowed to stand at 4° C. overnight. The reaction mixture was filtered and the filtrate was subjected to gel filtration on Sephadex ®G-75 (Pharmacia F.C.) using 10 mM aqueous ammonium bicarbonate as an eluent. The fraction containing the SOD derivative was lyophilized to give 8.52 mg of the SOD derivative as a white powder. The infrared absorption spectrum (KBr disk) of this product is shown in FIG. 3. The densitogram of the starting material SOD as determined by polyacrylamide electrophoresis (native PAGE) is shown in FIG. 4 (i) and that of the SOD derivative in FIG. 4 (ii). In the drawings, a represents SOD and b the SOD derivative.

The SOD derivative used in the following formulation examples was obtained according to Example of Synthesis 1. Comparable compositions are also obtainable by using other SOD derivatives according to this invention.

FORMULATION METHOD 1

The SOD derivative prepared in Example of Synthesis 1 is dissolved in distilled water (10 mg/ml) under ice cooling. The solution is adjusted to pH about 3.0 by dropwise addition of 0.5 M acetic acid and lyophilized. To the freeze-dried SOD derivative powder was added a medium/higher fatty acid glyceride supplemented with an amphiphilic agent and/or a lower alkanol and the mixture is shaken until a macroscopically uniform dispersion is obtained. The shaking treatment is carried out using the TOMY UR-150P chip-type supersonic wave generator (Tomy Seiki).

The duration of this treatment is not more than 30 seconds.

FORMULATION METHOD 2

A predetermined amount of an amphiphilic agent is added to a given quantity of distilled water and after addition of a lower alkanol as required, ultrasonic treatment is carried out to prepare a solution. Then, a solution (4 mg/ml) of SOD derivative powder (Example of Synthesis 1) in 0.02% aqueous ammonium carbonate solution, prepared under ice cooling, is added to the above solution in equal volumes and the mixture is lyophilized. To the resulting freeze-dried powder is added the medium/higher fatty acid glyceride, followed by addition of the lower alkanol as required. The mixture is ultrasonicated in an ice-water bath for 30 seconds.

The above procedure gave compositions of the invention as shown in Table 4.

TABLE 4

| Formulation No. | SOD derivative prepared in Example of Synthesis 1 | Medium/higher fatty acid glyceride | | Amphiphilic agent and/or lower alkanol | | Method of preparation |
|---|---|---|---|---|---|---|
| 1 | 1 mg | Panasate ®875 | 1 ml | Phosphatidylcholine | 0.1 g | 1 |
| 2 | 1 mg | Panasate ®810 | 0.95 ml | Unigli ® GO-206 | 0.05 ml | 2 |
| 3 | 1 mg | Panasate ®800 Olive oil | 0.25 ml 0.75 ml | Yolk lecithin | 0.1 g | 1 |
| 4 | 1 mg | ODO ® Linolic acid | 0.25 ml 0.75 ml | Soybean lecithin | 0.1 g | 1 |
| 5 | 1 mg | Panasate ®875 | 0.95 ml | Phosphatidylethanolamine Unigli ® GO-206 | 2 mg 0.05 ml | 2 |
| 6 | 1 mg | Panasate ®875 Homoteks ®PT | 0.8 ml 0.2 ml | Phosphatidylcholine | 2 mg | 2 |
| 7 | 1 mg | 10% ethanol-ODO ® | 1 ml | Yolk lecithin | 2 mg | 2 |
| 8 | 1 mg | Panasate ®810 | 0.95 ml | Phosphatidylethanolamine Unigli ®GO-206 | 0.1 g 0.05 ml | 2 |
| 9 | 1 mg | ODO ® | 1 ml | Soybean lecithin PEG 6000 | 0.1 g 0.1 g | 2 |
| 10 | 1 mg | Panasate ®800 | 0.9 ml | Tween ® 20 Span ®20 | 0.05 ml 0.05 ml | 2 |
| 11 | 1 mg | ODO ® | 1 ml | — | | 1 |
| 12 | 1 mg | Panasate ®800 | 1 ml | — | | 1 |
| 13 | 1 mg | Panasate ®810 | 1 ml | — | | 1 |
| 14 | 1 mg | Linolic acid | 1 ml | — | | 1 |
| 15 | 1 mg | Olive oil | 1 ml | — | | 1 |
| 16 | 1 mg | Panasate ®875 | 1 ml | — | | 1 |
| 17 | 1 mg | Edible oil [Nisshin Seiyu K.K.] | 1 ml | — | | 1 |
| 18 | 1 mg | ODO ® Edible oil [Nisshin Seiyu K.K.] | 0.5 ml 0.5 ml | — | | 1 |
| 19 | 1 mg | ODO ® Edible oil [Nisshin Seiyu K.K.] | 0.5 ml 0.5 ml | Phosphatidylcholine | 1 mg | 2 |
| 20 | 1 mg | ODO ® | 0.95 ml | Eison ® | 0.05 ml | 2 |
| 21 | 0.1 mg | ODO ® | 1 ml | — | | 1 |
| 22 | 10 mg | ODO ® | 1 ml | — | | 1 |
| 23 | 20 mg | ODO ® | 1 ml | — | | 1 |
| 24 | 30 mg | ODO ® | 1 ml | — | | 1 |
| 25 | 1 mg | Panasate ®875 | 1 ml | Unigli ® GO-206 Ethanol | 0.05 ml 0.15 ml | 1 |
| 26 | 1 mg | Panasate ®875 | 1 ml | Unigli ®GO-206 Ethanol | 0.05 ml 0.15 ml | 2 |

What is claimed is:

1. A method of treating an inflammatory disease which comprises administering to a patient with the disease a therapeutically effective amount of a superoxide dismutase derivative of the general formula

[SOD][Z]$_n$ wherein [SOD] represents a superoxide dismutase having 1 to 22 or 24 groups each derived from an amino group by removal of one hydrogen atom in lieu of amino groups; [Z] represents a monovalent copolymer group, constituting units of which are a group of the formula

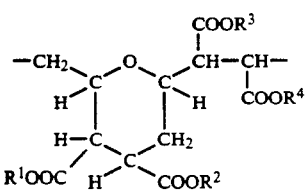

wherein $R^1$, $R^2$, $R^3$ and $R^4$ each represents a hydrogen atom or a residue group derived by removal of a hydroxyl from an alkanol of 1 to 8 carbon atoms, an ethylene glycol monoalkyl ether containing an alkyl moiety of 1 to 4 carbon atoms or a glycerin dialkyl ether containing alkyl moieties of 1 to 4 carbon atoms, provided that either $R^1$ or $R^2$ and either $R^3$ or $R^4$ each represents a hydrogen atom, and a residue derived from the group of the above-mentioned formula by removal of $OR^1$, $OR^2$, $OR^3$ or $OR^4$ group from one of its $COOR^1$, $COOR^2$, $COOR^3$ and $COOR^4$ groups (where the bond on the carbon atom of the carbonyl group is attached to [SOD]), said monovalent copolymer group having an average molecular weight of 500 to 200,000; and n represents an integer of 1 to 22 or 24 corresponding to the number of said groups each derived from an amino group by removal of one hydrogen atom in said [SOD], or a pharmaceutically acceptable salt thereof.

2. A pharmaceutically composition for oral administration comprising a superoxide dismutase derivative of the general formula

[SOD][Z]$_n$ wherein [SOD] represents a superoxide dismutase having 1 to 22 or 24 groups each derived from an amino group by removal of one hydrogen atom in lieu of amino groups; [Z] represents a monovalent copolymer group, constituting units of which are a group of the formula

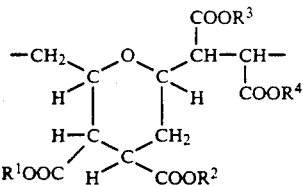

wherein $R^1$, $R^2$, $R^3$ and $R^4$ each represents a hydrogen atom or a residue derived by removal of a hydroxyl group from an alkanol of 1 to 8 carbon atoms, an ethylene glycol monoalkyl ether containing an alkyl moiety of 1 to 4 carbon atoms or a glycerin dialkyl ether containing alkyl moieties of 1 to 4 carbon atoms, provided that either $R^1$ or $R^2$ and either $R^3$ or $R^4$ each represents a hydrogen atom, and a residue derived from the group of the above-mentioned formula by removal of $OR^1$, $OR^2$, $OR^3$ or $OR^4$ group from one of its $COOR^1$, $COOR^2$, $COOR^3$ and $COOR^4$ groups (where the bond on the carbon atom of the carbonyl group is attached to [SOD]), said monovalent copolymer group having an average molecular weight of 500 to 200,000; and n represents an integer of 1 to 22 or 24 corresponding to the number of said groups each derived from an amino group by removal of one hydrogen atom in said [SOD] and/or a pharmaceutically acceptable salt and a medium/higher fatty acid glyceride.

3. The pharmaceutical composition of claim 2 wherein said medium/higher fatty acid glyceride is one or a mixture of triglycerides of fatty acids containing 6 to 20 carbon atoms.

4. The pharmaceutical composition of claim 3 wherein said medium/higher fatty acid glyceride is caprylic acid triglyceride, capric acid triglyceride or a mixture thereof.

5. A pharmaceutical composition for oral administration which comprises a superoxide dismutase derivative of the general formula

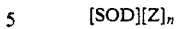

wherein [SOD] represents a superoxide dismutase having 1 to 22 or 24 groups each derived from an amino group by removal of one hydrogen atom in lieu of amino groups; [Z] represents a monovalent copolymer group, constituting units of which are a group of the formula

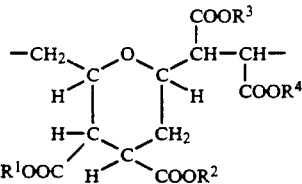

wherein $R^1$, $R^2$, $R^3$ and $R^4$ each represents a hydrogen atom or a residue derived by removal of a hydroxyl group from an alkanol of 1 to 8 carbon atoms, an ethylene glycol monoalkyl ether containing an alkyl moiety of 1 to 4 carbon atoms or a glycerin dialkyl ether containing alkyl moieties of 1 to 4 carbon atoms, provided that either $R^1$ or $R^2$ and either $R^3$ or $R^4$ each represents a hydrogen atom, and a residue derived from the group of the above-mentioned formula by removal of $OR^1$, $OR^2$, $OR^3$ or $OR^4$ group from one of its $COOR^1$, $COOR^2$, $COOR^3$ and $COOR^4$ groups (where the bond on the carbon atom of the carbonyl group is attached to [SOD]), said monovalent copolymer group having an average molecular weight of 500 to 200,000; and n represents an integer of 1 to 22 or 24 corresponding to the number of said groups each derived from an amino group by removal of one hydrogen atom in said [SOD] and/or a pharmaceutically acceptable salt thereof, a medium/higher fatty acid glyceride, and an amphiphilic agent and/or a lower alkanol.

* * * * *